United States Patent [19]

Moyers et al.

[11] Patent Number: 5,675,022
[45] Date of Patent: Oct. 7, 1997

[54] RECOVERY OF DIOXANONE BY MELT CRYSTALLIZATION

[75] Inventors: Charles Guthrie Moyers, Charleston, W. Va.; Michael Patrick Farr, Somerville, N.J.

[73] Assignee: Union Carbide Chemicals & Plastics Technology Corporation, Danbury, Conn.

[21] Appl. No.: 518,545

[22] Filed: Aug. 23, 1995

[51] Int. Cl.$^6$ .................................................. C07D 319/12
[52] U.S. Cl. ........................... 549/274; 549/378; 549/379
[58] Field of Search ................................. 549/274, 378, 549/379

[56] References Cited

U.S. PATENT DOCUMENTS

| | | | |
|---|---|---|---|
| 3,621,664 | 11/1971 | Saxer | 62/58 |
| 4,228,089 | 10/1980 | Bischof et al. | 260/428.5 |
| 5,230,769 | 7/1993 | Jancic et al. | 156/619 |
| 5,243,093 | 9/1993 | Kissinger et al. | 568/724 |
| 5,275,227 | 1/1994 | Staub | 164/122.1 |
| 5,326,541 | 7/1994 | Ulrich et al. | 422/254 |
| 5,326,887 | 7/1994 | Di Cosimo et al. | 549/274 |
| 5,338,519 | 8/1994 | Jancic et al. | 422/253 |
| 5,362,900 | 11/1994 | Kissinger et al. | 558/265 |
| 5,391,768 | 2/1995 | Jiang | 549/274 |
| 5,430,194 | 7/1995 | Barner et al. | 568/429 |
| 5,434,316 | 7/1995 | Kissinger | 568/724 |
| 5,539,081 | 7/1996 | Gruber et al. | 528/354 |

OTHER PUBLICATIONS

"Oxidation Inhibition In Organic Materials", vol. II, Chapter 7, Jan Pospisil And Peter P. Klemchuk, pp. 299–346, CRC Press, Inc. (1990).

*Primary Examiner*—Johann Richter
*Assistant Examiner*—Laura R. Cross
*Attorney, Agent, or Firm*—W. K. Volles

[57] ABSTRACT

Processes are disclosed for the recovery of 1,4-dioxanone by melt crystallization from a feed containing impurities capable of initiating the polymerization of 1,4-dioxanone, e.g., diethylene glycol. The processes of the present invention utilize melt crystallization in a cyclic process involving the steps of (i) crystallizing the 1,4-dioxanone out of the feed at a temperature below its melting point and removing a liquid residue containing a higher concentration of impurities, (ii) partially melting the crystallized 1,4-dioxanone to further remove impurities and (iii) thereafter, melting the remaining crystallized 1,4-dioxanone and recovering the melted product. The crystallization process can be repeated as required to achieve the desired purity. The purity of the product obtained is typically 99.5 wt %, 1,4-dioxanone or higher. The purified 1,4-dioxanone is useful, for example, as a monomer in the production of polydioxanone.

12 Claims, 1 Drawing Sheet

RECOVERY OF DIOXANONE BY MELT CRYSTALLIZATION

FIELD OF THE INVENTION

The present invention relates to the purification of 1,4-dioxanone, and more specifically relates to processes for the recovery of 1,4-dioxanone from feeds by melt crystallization.

BACKGROUND OF THE INVENTION

The compound 1,4-dioxanone (also referred to in the art as "p-dioxanone") has utility, for example, as a monomer in the production of polydioxanone. Polydioxanone can be used to make a variety of commercially useful products particularly where biodegradability is desired, such as, for example, fibers, e.g., sutures, molded articles, e.g., containers, medical devices and surgical clips, and films, e.g., compostable trash bags.

Various methods are known for the manufacture of p-dioxanone. One method is by reacting ethylene glycol or diethylene glycol, metallic sodium and chloroacetic acid. Another method is by reacting ethylene glycol, formaldehyde and carbon monoxide. Still another method is by oxidizing dioxanone. Often p-dioxanone is made by the continuous, gas phase dehydrogenation of diethylene glycol. As a result, the p-dioxanone product typically contains some diethylene glycol. Similarly, when one of the other reaction routes described above is used, the product can contain some of the starting materials. Certain of these starting materials are detrimental in that they are capable of initiating, i.e., catalyzing, the polymerization of p-dioxanone. In fact, diethylene glycol is commonly used as an initiator in the polymerization of p-dioxanone. Examples of other impurities which are capable of initiating the polymerization of p-dioxanone, and are typically found in the p-dioxanone product, include for example, hydroxy containing compounds such as water, ethylene glycol and hydroxy acids, e.g., hydroxy acetic acid and hydroxyethoxy acetic acid. Thus, controlling the amount of diethylene glycol and such other hydroxyl-containing impurities is critical in order to obtain the desired molecular weight of polydioxanone.

The amount of diethylene glycol and other impurities in the p-dioxanone product can vary depending on the reaction conditions. Therefore, it is usually desirable to remove substantially all of the diethylene glycol and other impurities from the p-dioxanone and reintroduce the desired amount of diethylene glycol or other initiators for the polymerization reaction. However, the removal of such impurities presents a unique problem in that the impurities themselves can cause polymerization of the p-dioxanone to occur during the removal process.

Solvent crystallization has been proposed as a method for purifying p-dioxanone. Solvent crystallization involves dissolving the contaminated stream containing 1,4-dioxanone in a suitable solvent, such as, for example, ethyl acetate, cooling the solution to a temperature effective to promote the formation of crystals, e.g., −20° C., and generating crystals by known methods, such as, for example, introducing pure 1,4-dioxanone crystals (known in the art as "seeding"). After the crystals of 1,4-dioxanone have formed, the mixture is filtered and washed to recover the crystals of 1,4-dioxanone. Multiple recrystallizations can be conducted as desired in order to obtain the desired purity. However, solvent crystallization can often be inefficient because of the necessity to use organic solvents, water extraction, slurry handling, centrifugation, filters, vacuum systems, dryers and the like.

Accordingly, new processes are desired for the recovery of p-dioxanone from feeds containing impurities which are capable of initiating the polymerization of 1,4-dioxanone.

SUMMARY OF THE INVENTION

By the present invention new processes are provided for the recovery of 1,4-dioxanone from feeds which contain impurities that are capable of initiating the polymerization of 1,4-dioxanone. Quite advantageously, the processes of the present invention do not require the use of organic solvents, water extraction, slurry handling, centrifugation, filters, vacuum systems or dryers. The processes of the present invention utilize melt crystallization in a cyclic process involving the steps of(i) crystallizing the 1,4-dioxanone out of the feed at a temperature below its melting point and removing a liquid residue containing a higher concentration of impurities, (ii) partially melting the crystallized 1,4-dioxanone to further remove impurities and (iii) thereafter, melting the remaining crystallized 1,4-dioxanone and recovering the melted product. The crystallization process can be repeated as required to achieve the desired purity and recovery.

Quite surprisingly, it has been found that melt crystallization can be used in accordance with the present invention to provide high purity p-dioxanone, e.g., 99.5% or greater, while having substantially no polymerization of the p-dioxanone occurring in the product from the process despite the presence of impurities which are initiators for the polymerization reaction.

DETAILED DESCRIPTION OF THE INVENTION

Figure 1:
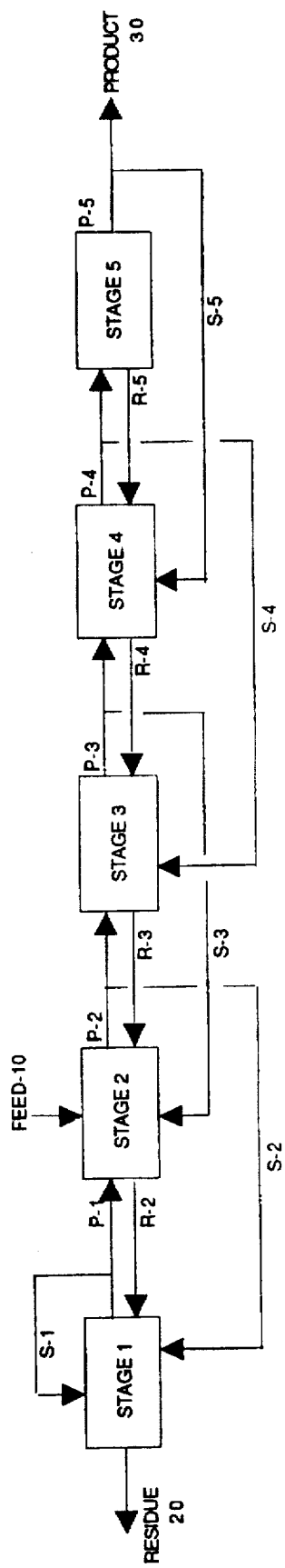
FIG. 1 illustrates a preferred operational schematic of the processes of the present invention.

Feeds suitable for use in accordance with the present invention, comprise p-dioxanone. Typically, the source of the feed is the reaction product from the production of p-dioxanone which can be prepared by various methods known to those skilled in the art, one of which is by reacting diethylene glycol (sometimes referred to herein as "DEG") in the vapor phase in the presence of a metal catalyst, e.g., copper chromite, under an elevated temperature, e.g., 200°–300° C. Further details concerning the manufacture of p-dioxanone are known to those skilled in the art.

The concentration of p-dioxanone in the feed can range from about 25 to 99.5 wt %, typically from about 35 to 99.5 wt %, preferably from about 60 to 99.5 wt %, more preferably from about 85 to 99.5 wt %, and most preferably from about 90 to 99.5 wt %, based upon the total weight of p-dioxanone in the feed. The reaction product from the manufacture of p-dioxanone is often bulk purified in a distillation column to provide a feed containing about 99.5 wt % 1,4-dioxanone based on the total weight of the feed. When recovery stages are employed in the crystallization (as hereinafter described), the concentration of p-dioxanone to such stages may be at the lower end of the above-stated ranges.

The feed also contains at least one impurity capable of initiating the polymerization of p-dioxanone. Examples of such impurities are those selected from the group consisting of ethylene glycol, diethylene glycol, water, and hydroxy acids, e.g., hydroxy acetic acid and hydroxyethoxy acetic acid. Such impurities may be present in the feed at a concentration, for example, of from about 0.5 to 75 wt %, preferably from about 0.5 to 70 wt. % and more preferably from about 0.1 to 10 wt %, based on the total weight of the feed. Typically, diethylene glycol is the major impurity among the group when diethylene glycol is used as a reactant and is present at a concentration of from 0.1 to 25 wt. % based on the total weight of the feed.

In the processes of the present invention, the feed is contacted in a molten state with a crystallization surface having a temperature below the melting point of the p-dioxanone, e.g., from about −20° C. to 30° C., to solidify a fraction of the feed comprising the p-dioxanone. Quite surprisingly, the impurities, e.g., diethylene glycol, substantially remain in the liquid phase and do not crystallize with the p-dioxanone. Thus, the impurities are removed with the unsolidified liquid residue.

Preferably, after the feed is crystallized, the temperature of the solidified crystals of p-dioxanone is increased to a temperature effective to cause the outer surface of the crystals to melt (known in the art as "sweating"). This sweating process causes additional impurities which are entrapped in the solidified p-dioxanone to melt and thus be removed.

After the sweating process is completed, the remaining portion of the crystallized p-dioxanone is melted and recovered as product. This recovered product can then be recrystallized as many times as necessary in order to achieve the desired purity.

In general, any equipment suitable for conducting melt crystallization can be used in the processes of the present invention. A variety of types of commercial equipment is available. For example, some melt crystallization equipment is designed to pump the feed upward through tubes or chambers which comprise the crystallization surface. Other equipment is designed in the form an endless belt or conveyor which transports the feed from a crystallization chamber to a melt chamber. Equipment preferred for use in accordance with the present invention is that which provides a downward flow of the feed over the crystallization surface (referred to in the art as "falling film crystallization"). This equipment typically comprises a group of tubes with a central distribution system to each tube, separate liquid circulation systems for the feed and the heat exchange medium, circulation pumps, a collecting tank in communication with the bottom of the tubes and holding tanks for the feeds and effluent from each stage. Such equipment is available, for example, from Sulzer Chemtech, Toronto, Canada. Further details concerning the equipment for conducting melt crystallization are known to those skilled in the art.

The invention is further described with reference to the drawing which illustrates a preferred aspect of the present invention. The following description is not intended to be limiting on the scope of the claims which follow.

In FIG. 1, each Stage, i.e., Stage 1 to Stage 5, represents the sequential occurrence of the cyclic process described above, i.e., crystallization, sweat and melt, in the apparatus. The designation "P" refers to melt product from the cycle advanced to the subsequent stage. The designation "S" refers to sweat from the cycle, recycled to the previous stage. The designation "R" refers to residue from the cycle, recycled to the previous stage.

A feed (10) comprising p-dioxanone and diethylene glycol is introduced to a holding tank (not shown) designated for Stage 2. Also introduced to the holding tank are product from Stage 1 (P-1), sweat from Stage 3 (S-3) and residue from Stage 3 (R-3) as hereinafter described. The material in the holding tank for Stage 2 is then introduced into the collection tank of the apparatus. The collection tank is maintained at a temperature effective to maintain the material in the liquid state without causing polymerization of the p-dioxanone in the presence of the DEG, e.g., 30° to 50°° C. The pressure during the entire process is not critical and is typically maintained at about atmospheric pressure, e.g., 0.8 to 1.2 atmospheres. Preferably, the process is conducted in a dry, inert atmosphere, e.g., under nitrogen, in order to keep the product dry.

The material in the collecting tank is then circulated through the circulation system to the central distribution system and then downward through the inside of each tube, i.e., the internal surfaces of the tubes comprise the crystallization surface. The circulation rate is typically at least about 250 pounds ("lb") per hour per linear foot ("ft"), i.e., circumference of the tube through which the liquid is passing, and preferably ranges from about 1300 to 1500 lb per hour per linear ft and is sufficient to promote the formation of a film flowing down the internal surfaces of the tubes and also sufficient to provide a residence time which is low enough to avoid polymerization of the p-dioxanone in the presence of the impurities. After circulation has been established, the temperature of the crystallization surface is lowered by the introduction of a suitable coolant, e.g., propylene glycol, along the outer surfaces of the tubes, preferably in a direction concurrent to the flow of the feed material. The temperature of the crystallization surface is reduced until a film of crystalline material forms on the inside walls of the tubes. This initial temperature is often referred to as the initial crystallization temperature ("ICT") of the feed. For the processes of the present invention, the ICT is typically from about 15° to 30° C. After a film of crystals has formed over substantially the entire crystallization surface, the temperature of the film is preferably further reduced by about 1° to 15° C. and the circulation flow is continued until a buildup of crystals to a thickness of about 5 to 25 millimeters, preferably from about 10 to 15 millimeters, is obtained on the crystallization surface. The unsolidified liquid collected during the crystallization step is removed from the collection tank as residue (R-2) and processed during Stage 1 as hereinafter described. This completes the crystallization step of the process. The crystallization step typically occurs over a time period of from about 10 to 90 minutes and preferably from about 15 to 30 minutes.

Upon completion of the crystallization step, the feed circulation is discontinued and the temperature of the crystallization surface is gradually increased to a temperature effective to cause a partial melting of the crystals, i.e., sweating, e.g., about 15° to 30° C. It is preferred that the temperature employed during the sweating step is effective to cause a portion of the crystals to melt without causing polymerization of the p-dioxanone in the presence of the initiator. Typically, a portion of from about 5 to 20 wt % of the crystals is melted during the sweating step. The effluent from the sweating step (S-2) is collected in the collection tank and passed to the holding tank for Stage 1 as hereinafter described. The time period for conducting the sweating step typically ranges from about 5 to 30 minutes, preferably from about 10 to 20 minutes.

Upon completion of the sweating step, the temperature of the crystallization surface is then either maintained at the sweating temperature of further increased to a temperature effective to melt the remainder of the crystals at the desired rate, e.g., about 10° to 30° C. It is preferred that this melt temperature be sufficient to cause the crystals to melt without causing polymerization of p-dioxanone in the presence of the initiator. The time period for conducting the melt step typically ranges from about 5 to 60 minutes, preferably from about 10 to 20 minutes. The product melt from the melting step (P-2) is collected in the collection tank and passed to the holding tank for Stage 3 as hereinafter described.

In Stage 1, residue from Stage 2 (P-2), sweat from Stage 2 (S-2) and sweat from Stage 1 (S-1), all of which is contained in the holding tank for Stage 1, are processed through the steps of crystallization, sweating and melt, as described above with reference to Stage 2. Hence, the feed to Stage 1 is typically of lower purity than the feed to the process. The purpose for conducting the process in Stage 1 is to enhance the recovery of p-dioxanone from the residue of Stage 2 (R-2). Thus, Stage 1 may be referred to as a "recovery stage", whereas Stages 2 to 5 may be referred to as "purification stages". A residue (20) which is rich in DEG relative to the feed is obtained from Stage 1 and removed from the process.

In Stage 3, product from Stage 2 (P-2) residue from Stage 4 (R-4) and sweat from Stage 4 (S-4), all of which are contained in the holding tank for Stage 3, are processed through the steps of crystallization, sweat and melt as described with reference to Stage 2. The product from Stage 3 (P-3) is passed to the holding tank for Stage 4. The residue from Stage 3, (R-3) and the sweat from Stage 3 (S-3) are passed to the holding tank for Stage 2 as described above.

In Stage 4, the product from Stage 3 (P-3), the sweat from Stage 5 (S-5) and the residue from Stage 5 (R-5) all of which are contained in the holding tank for Stage 4 are processed through the steps of crystallization, sweat and melt as described with respect to Stage 2. Product from Stage 4, (P-4) is passed to the holding tank for Stage 5. The residue from Stage 4, (R-4) and the sweat from Stage 4 (S-4) are passed to the holding tank for Stage 3 as described above.

In Stage 5, product from Stage 4 (P-4) is processed through the steps of crystallization, sweat and melt as described above with reference to Stage 2. The residue from Stage 5, (R-5) and the sweat from Stage 5, (S-5) are passed to the holding tank for Stage 4 as described above. The product from Stage 5 is withdrawn from the process as product (30).

Typically the purity of the product is substantially greater than the purity of the feed. Often the concentration of p-dioxanone in the product is at least 90 wt %, preferably at least 99 wt %, more preferably at least 99.5 wt % and most preferably at least 99.9 wt %, based on the total weight of the product. Typically, the overall recovery of p-dioxanone from the process, i.e., over all stages, is at least 10 wt %, preferably at least 50 wt % and more preferably at least 90 wt % The overall recovery is calculated by dividing the amount of p-dioxanone in the product, e.g., line 30, by the amount of p-dioxanone in the feed, e.g., line 10. Preferably, substantially none of the p-dioxanone is polymerized to polydioxanone in the product from the processes of the present invention. Thus, the concentration of polydioxanone in the product from the process is less than 1 wt %, more preferably less than 0.1 wt % based on the total weight of the product. In the residue from the process, some polydioxanone may be present, e.g., typically less than 10 wt %, preferably less than 5 wt % and more preferably less than 1 wt % based on the total weight of the residue.

The p-dioxanone products obtained from the processes of the present invention have utility, for example, as monomers in the polymerization of polydioxanone or as chemical intermediates for the synthesis of other compounds or derivatives. When polydioxanone is manufactured from the p-dioxanone of the present invention, it is preferred that an antioxidant, e.g., those selected from the group consisting of hindered phenols, phosphites, phosphines, and phosphonites, thioethers, arylamines, hindered amines, hydroxyl amines or mixtures thereof be employed in order to inhibit oxidative degradation of the polymer. Such polymers made from the p-dioxanone can be used in the fabrication of a wide variety of products including, for example, sheets, films, e.g., trash bags, fibers, e.g., sutures, fishing line and non-woven fabrics, and molded articles, e.g., containers, tools and medical devices, e.g., staples, clips, pins, prostheses, etc. In such products the extent of biodegradability can be controlled by the use of hydrolytic stabilizers or ultraviolet stabilizers known to those skilled in the art. Further details concerning uses for p-dioxanone are known to those skilled in the art.

The following Examples are provided for illustrative purposes and are not intended to limit the scope of the claims which follow.

The following ingredients were used in the Examples.

DEG-diethylene glycol available from Union Carbide Corporation, Danbury, Conn.

Cu 1186T-a barium promoted, copper chromite catalyst available from Engelhard Corporation, Elyria, Ohio.

DABCO T9-tin octoate available from Air Products, Allentown, Pa.

Irganox 1010- a tetrakis[methylene(3,5-di-tert-butyl-4-hydroxyhydrocinnamate)]methane antioxidant available from Ciba-Geigy, Hawthorne, N.Y.

Tone® P-787-polycaprolactone having a weight average molecular weight of 80,000 g/gmole available from Union Carbide, Danbury, Conn.

All buffers and standards for ASTM 533 are available from Aldrich Chemical Company, Inc., Milwaukee, Wis.

EXAMPLE 1

MANUFACTURE OF P-DIOXANONE

About 2000 g of diethylene glycol, in a continuous flow of about 500 g per hour, were passed in a vapor state into a reaction chamber which contained about 1400 g of barium promoted, Cu 1186T catalyst. The reaction temperature was maintained between 220° and 280° C. The vapor was passed through the chamber and condensed. The condensate contained 1733 g of 1,4-dioxanone, 622 g of unreacted DEG. The product was converted at a conversion of 68.9 percent (moles of DEG in minus moles of DEG out divided by moles of DEG in) with a corresponding yield of 86.6 percent (weight of 1,4-dioxanone out divided by weight of DEG in).

EXAMPLE 2

PURIFICATION BY MELT CRYSTALLIZATION

A solution (750.2 g) consisting of 99.05 weight percent 1,4-dioxanone and impurities (mostly unreacted diethylene glycol) measured by gas chromatographic analysis was produced in accordance with the procedure set forth in Example 1.

A laboratory falling film crystallizer was used in order to purify the reaction product described above. The crystallizer comprised a two liter crystallizer kettle fitted with a heating element, a one inch ID by one meter tall jacketed vertical tube, an exit port for recycling residue, recycle heaters, a feed pump, a film distributor and a coolant system for the jacketed section of the vertical tube. A schematic of this apparatus is shown in FIG. 6 of U.S. Pat. No. 5,430,194.

The procedure used to purify the product was as follows: Approximately 1500 cc of the above described solution comprising p-dioxanone and impurities were charged to the crystallizer kettle. The kettle was then heated to slightly above its freezing point, e.g., 30° C. The solution was then circulated out of the exit port through the recycle heaters, into the feed pump, out from the feed pump, into the film distributor, out of the film distributor and allowed to pass downward along the inside surface of the falling film crystallizer back to the crystallizer kettle. The circulation rate was set at about 1000 cc per minute. The falling film crystallizer was then cooled by decreasing the temperature of the coolant, i.e., propylene glycol/water 50/50% by weight, circulating through the jacket to a temperature of about 15° to 20° C. until a film of crystalline material formed on the inside walls of the falling film crystallizer, i.e., the ICT. Circulation was maintained at the ICT for 5 minutes and then the temperature of the coolant was gradually reduced until about 80% of the feed in the kettle was depleted. At that point, the material buildup on the internal walls of the crystallizer was approximately one-fourth of an inch thick. Throughout this time the crystallizer kettle was maintained slightly above the freezing point of the material.

After the cooling cycle was completed, the remainder of the product solution in the crystallizer kettle was discharged and then the temperature of the coolant was gradually increased until a portion of the crystals started to melt, i.e., sweat, i.e., about 30° C. Approximately 50 cc of material was collected during the sweating cycle and removed from the crystallizer kettle. Then the remainder of the product was melted and collected in the crystallizer kettle. About 371.2 grams of residue were obtained having a composition of 98.34 weight percent 1,4-dioxanone. The sweat (63.02 g) contained 99.39 weight percent 1,4-dioxanone. The product melt (314.88 g) contained 99.96 weight percent 1,4-dioxanone.

EXAMPLE 3

MANUFACTURE OF POLYDIOXANONE

About 611 g of dry, highly purified p-dioxanone (99.5±% pure) and 3.05 g of Irganox 1010 was charged to an oven dried, 1000 ml, three neck flask fitted with a dry argon purge and an overhead agitator. The flask was lowered into an oil bath and the temperature was raised to 110° C. As the material temperature approached 90° C., 0.28 ml of diethylene glycol and 0.27 ml of a 13.74% solution of T9 in toluene was charged to the reactor. The mixture was allowed to react for 280 minutes. The melt was discharged from the reactor into trays and put into a desiccator to cool.

Into a 500 ml three neck flask setup as described above was charged with 100.75 g of the polymer made in Example 1. To the polymer was added 0.50 g of Irganox 1010. The mixture was heated to 118° C. and mixed for 30 minutes. The mixture was discharged from the reactor into aluminum trays.

Both the polymers obtained from the reactions described above were placed in a vacuum oven at 70° C. with an argon purge and 28 mm of Hg vacuum and dried overnight to remove residual monomer.

The polydioxanone so produced can then be extruded or molded into desired forms, such as, for example, sheets, fibers, pellets, films and the like. The details of such operations are known to those skilled in the art.

Those skilled in the art will recognize that other aspects of the invention are intended to be included within the scope of the claims which follow. For example, additional steps., e.g., other partial meltings, can be added to the process. Also, other flow configurations of the sweat and residue fractions can be employed in addition to those specifically referred to herein. Also, the process can be combined with other unit operations, e.g., distillation, either prior to or subsequent to crystallization. Also, in addition to the impurities specifically recited, other impurities such as, for example, those which can cause color, odor, reactivity or stability problems in the p-dioxanone or products made therefore, e.g., polydioxanone, can be removed by the processes of the present invention.

We claim:

1. A cyclic process for recovering 1,4-dioxanone from a feed containing 1,4-dioxanone and at least one impurity which is an initiator for the polymerization of 1,4-dioxanone, said process comprising:

(a) contacting the feed in a molten state with a crystallization surface;

(b) cooling the crystallization surface to a crystallization temperature below the melting point of the 1,4-dioxanone and effective to cause the formation of crystals on the crystallization surface comprising 1,4-dioxanone in a higher concentration than in the feed and withdrawing a liquid residue fraction comprising 1,4-dioxanone in a lower concentration than in the feed;

(c) discontinuing passing the feed to the crystallizer surface and heating the crystallizer surface to a sweat temperature at or above the melting point of the 1,4-dioxanone and effective to cause a portion of the crystals to melt and form a sweat fraction, without causing the polymerization of the 1,4-dioxanone in the presence of the impurity;

(d) withdrawing the sweat fraction and heating the crystallizer surface to a melt temperature above the melting point of the 1,4-dioxanone and effective to cause the remaining portion of the crystals to melt and form a product fraction, without causing the polymerization of the 1,4-dioxanone in the presence of the impurity; and (e) withdrawing the product fraction.

2. The process of claim 1 wherein the impurity is selected from the group consisting of ethylene glycol, diethylene glycol, water, or hydroxy acids.

3. The process of claim 1 wherein the feed comprises at least about 85 wt. % 1,4-dioxanone based on the total weight of the feed.

4. The process of claim 1 wherein the crystallization temperature is from about 15° to 30° C.

5. The process of claim 1 wherein the sweat temperature is from about 15° to 30° C.

6. The process of claim 1 wherein the melt temperature is from about 15° to 30° C.

7. The process of claim 1 further comprising repeating steps (a), (b), (d) and (e) on the product fraction.

8. The process of claim 1 further comprising repeating steps (a), (b), (d) and (e) on the residue fraction.

9. The process of claim 8 further comprising introducing at least a portion of the sweat fraction along with the residue fraction to step (a).

10. The process of claim 1 wherein the process is conducted in a nitrogen atmosphere.

11. The process of claim 1 wherein the product fraction contains less than 1.0 wt % poly 1,4-dioxanone based on the total weight of the fraction.

12. The process of claim 1 wherein the product fraction comprises at least 99.9 wt % 1,4-dioxanone based on the total weight of the product fraction.

* * * * *